United States Patent [19]
Adair

[11] Patent Number: 6,086,528
[45] Date of Patent: Jul. 11, 2000

[54] SURGICAL DEVICES WITH REMOVABLE IMAGING CAPABILITY AND METHODS OF EMPLOYING SAME

[76] Inventor: Edwin L. Adair, 317 Paragon Way, Castle Pine Village, Colo. 80104

[21] Appl. No.: 08/927,785

[22] Filed: Sep. 11, 1997

[51] Int. Cl.[7] .................................................. A61B 1/05
[52] U.S. Cl. ........................ 600/104; 600/110; 600/129; 600/130
[58] Field of Search .................................. 600/104, 105, 600/102, 112, 114, 115, 116, 182, 129, 109, 160, 110, 130; 348/65, 71, 76

[56] References Cited

U.S. PATENT DOCUMENTS

| | | | |
|---|---|---|---|
| 3,294,085 | 12/1966 | Wallace | 600/182 |
| 4,027,510 | 6/1977 | Hiltebrandt | 600/104 |
| 4,249,533 | 2/1981 | Komiya | 128/303.1 |
| 4,300,564 | 11/1981 | Furihata | 600/104 |
| 4,604,992 | 8/1986 | Sato | 600/109 |
| 4,718,423 | 1/1988 | Willis et al. | 600/325 |
| 4,759,348 | 7/1988 | Cawood | 600/104 |
| 4,762,120 | 8/1988 | Hussein | 128/6 |
| 4,777,524 | 10/1988 | Nakajima | 600/168 |
| 4,782,819 | 11/1988 | Adair | 600/109 |
| 4,798,193 | 1/1989 | Giesy | 600/114 |
| 4,878,485 | 11/1989 | Adair | 128/6 |
| 4,878,893 | 11/1989 | Chin | 600/114 |
| 4,898,586 | 2/1990 | Furukawa | 600/110 |
| 4,918,521 | 4/1990 | Yabe et al. | 600/109 |
| 4,945,895 | 8/1990 | Takai | 600/104 |
| 5,035,248 | 7/1991 | Zinnecker | 128/751 |
| 5,116,317 | 5/1992 | Carson, Jr. et al. | 600/116 |
| 5,152,277 | 10/1992 | Honda et al. | 600/116 |
| 5,166,787 | 11/1992 | Irion | 358/98 |
| 5,188,596 | 2/1993 | Condon et al. | 604/101 |
| 5,191,879 | 3/1993 | Krauter | 600/109 |
| 5,197,978 | 3/1993 | Hess | 623/1 |
| 5,222,477 | 6/1993 | Lia | 128/6 |
| 5,251,613 | 10/1993 | Adair | 128/6 |
| 5,263,928 | 11/1993 | Trauthen et al. | 600/129 |
| 5,278,642 | 1/1994 | Danna et al. | 600/181 |
| 5,290,284 | 3/1994 | Adair | 606/37 |
| 5,329,940 | 7/1994 | Adair | 128/200.26 |
| 5,402,768 | 4/1995 | Adair | 128/4 |
| 5,411,016 | 5/1995 | Kume et al. | 600/116 |
| 5,489,256 | 2/1996 | Adair | 600/133 |
| 5,494,483 | 2/1996 | Adair | 600/111 |
| 5,495,114 | 2/1996 | Adair | 257/59 |
| 5,536,234 | 7/1996 | Newman | 600/104 |
| 5,630,782 | 5/1997 | Adair | 600/133 |
| 5,662,585 | 9/1997 | Willis | 600/104 |
| 5,667,472 | 9/1997 | Finn | 600/182 |
| 5,667,478 | 9/1997 | McFarlin | 600/182 |
| 5,681,262 | 10/1997 | Isse | 600/104 |
| 5,716,321 | 2/1998 | Kerin | 600/114 |
| 5,746,692 | 5/1998 | Bacich | 600/114 |
| 5,746,770 | 5/1998 | Zeitels | 600/182 |
| 5,762,604 | 6/1998 | Kieturakis | 600/104 |
| 5,873,816 | 2/1999 | Kagawa et al. | 600/110 |
| 5,962,842 | 10/1999 | Kimura | 348/76 |

FOREIGN PATENT DOCUMENTS

| | | |
|---|---|---|
| 2847633 | 2/1978 | Germany . |
| 880331620 | 11/1990 | Japan . |
| 5-228109 | 9/1993 | Japan .................. 600/118 |

*Primary Examiner*—John P. Leubecker
*Attorney, Agent, or Firm*—Fields and Johnson, P.C.

[57] ABSTRACT

Surgical devices with removable imaging capability and methods are disclosed. The imaging capability for the surgical devices are provided by a very small microendoscope having processor circuitry at the distal end for providing a video ready signal to a monitor. Because of the small size of the microendoscope, it can be used in conjunction with many surgical instruments which traditionally do not have integral imaging capability. In one application, the microendoscope may be used with Jackson grasping forceps. In another application, the microendoscope may be used with either a stent placement catheter or balloon catheter. In yet another application, the microendoscope may be used with an over-tube tissue separating, dissecting or fulgeration device. The application of the microendoscope with each of the above surgical instruments results in a unique method of performing a surgical task by providing imaging capability throughout all stages of introducing and removing the instruments from within the body of a patient.

19 Claims, 5 Drawing Sheets

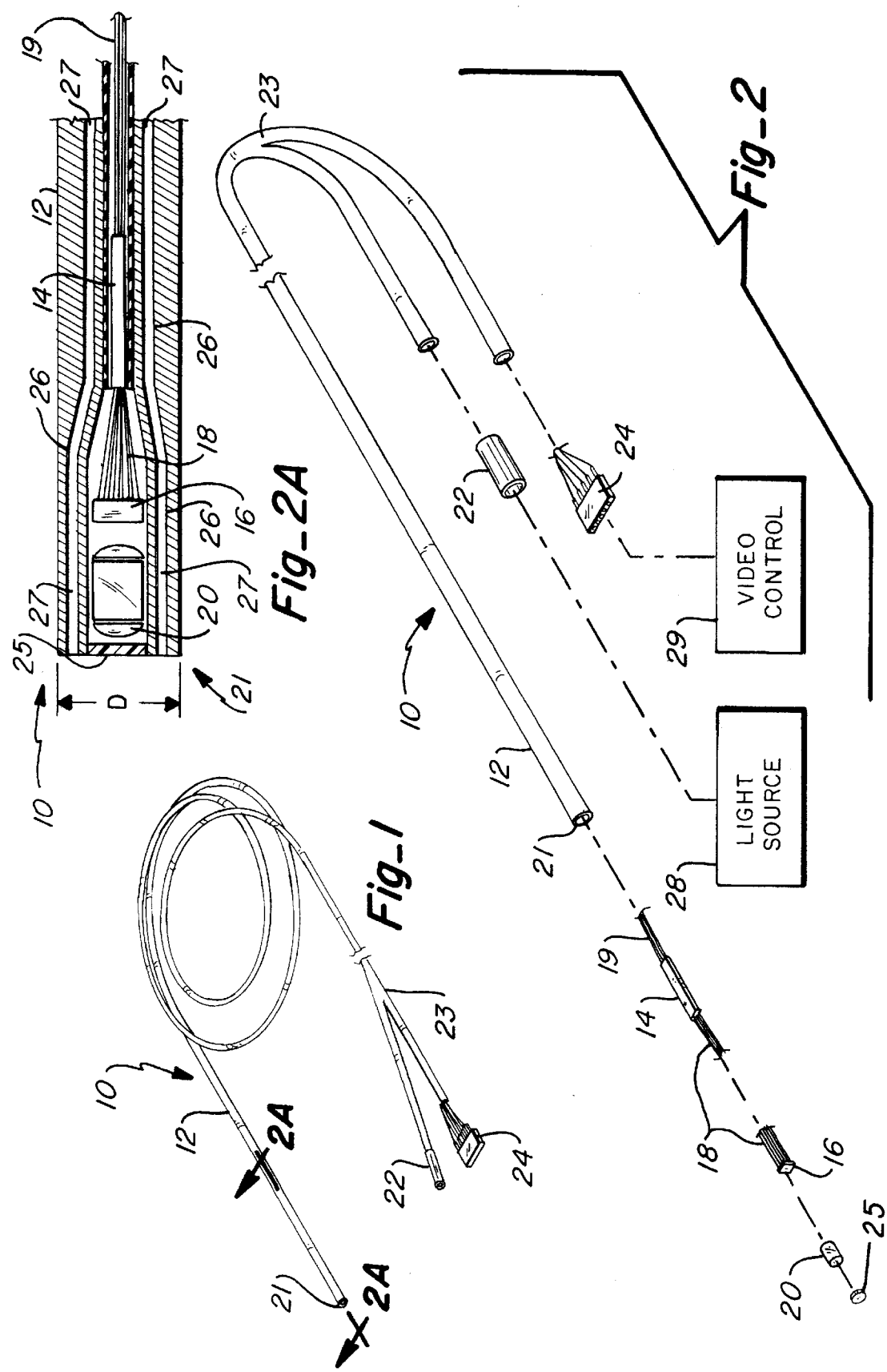

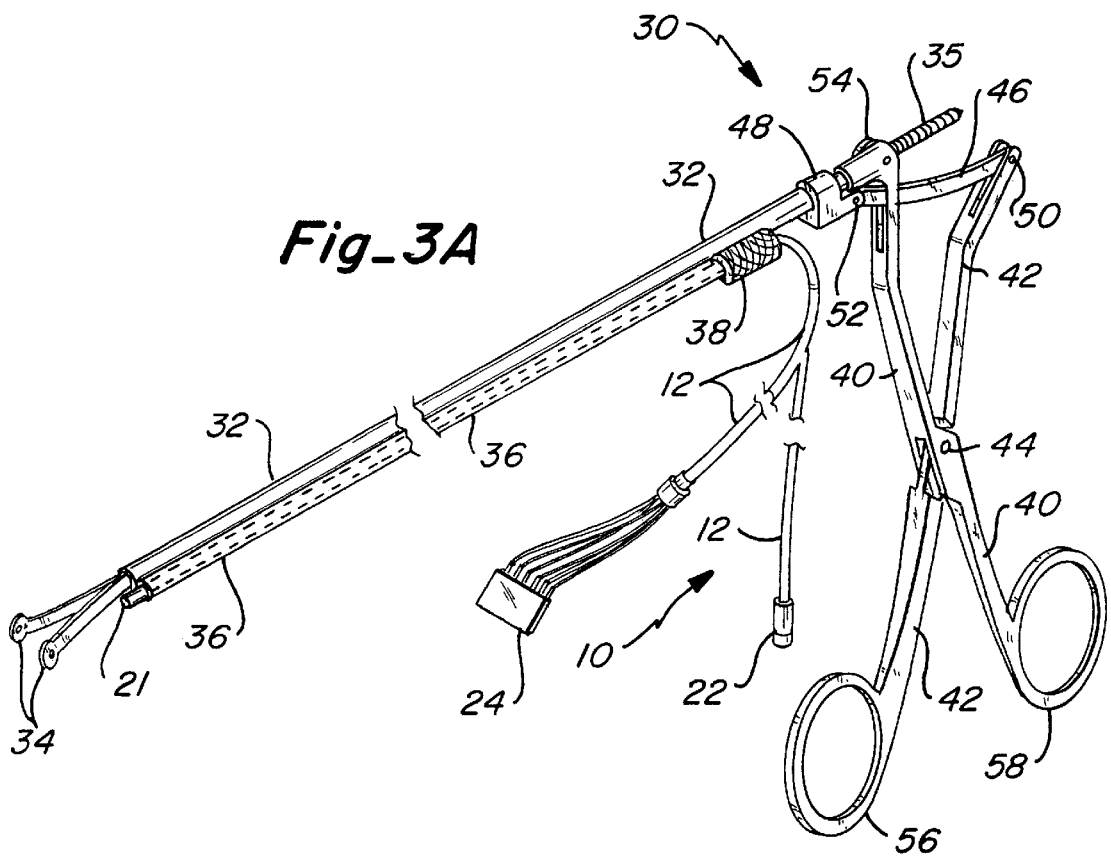
Fig_3A
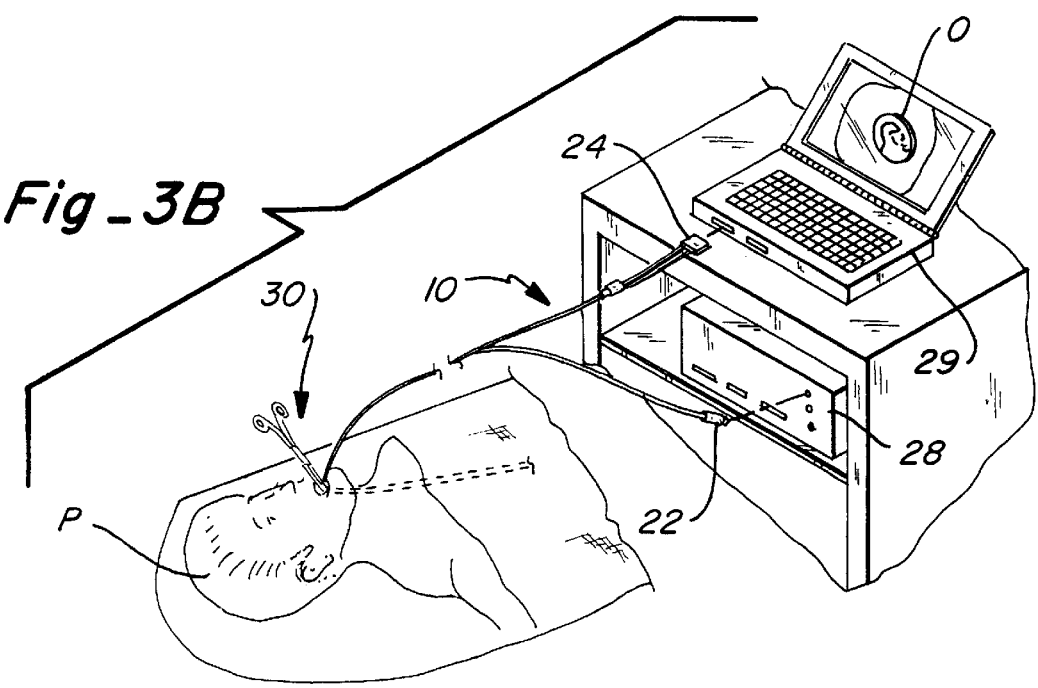
Fig_3B

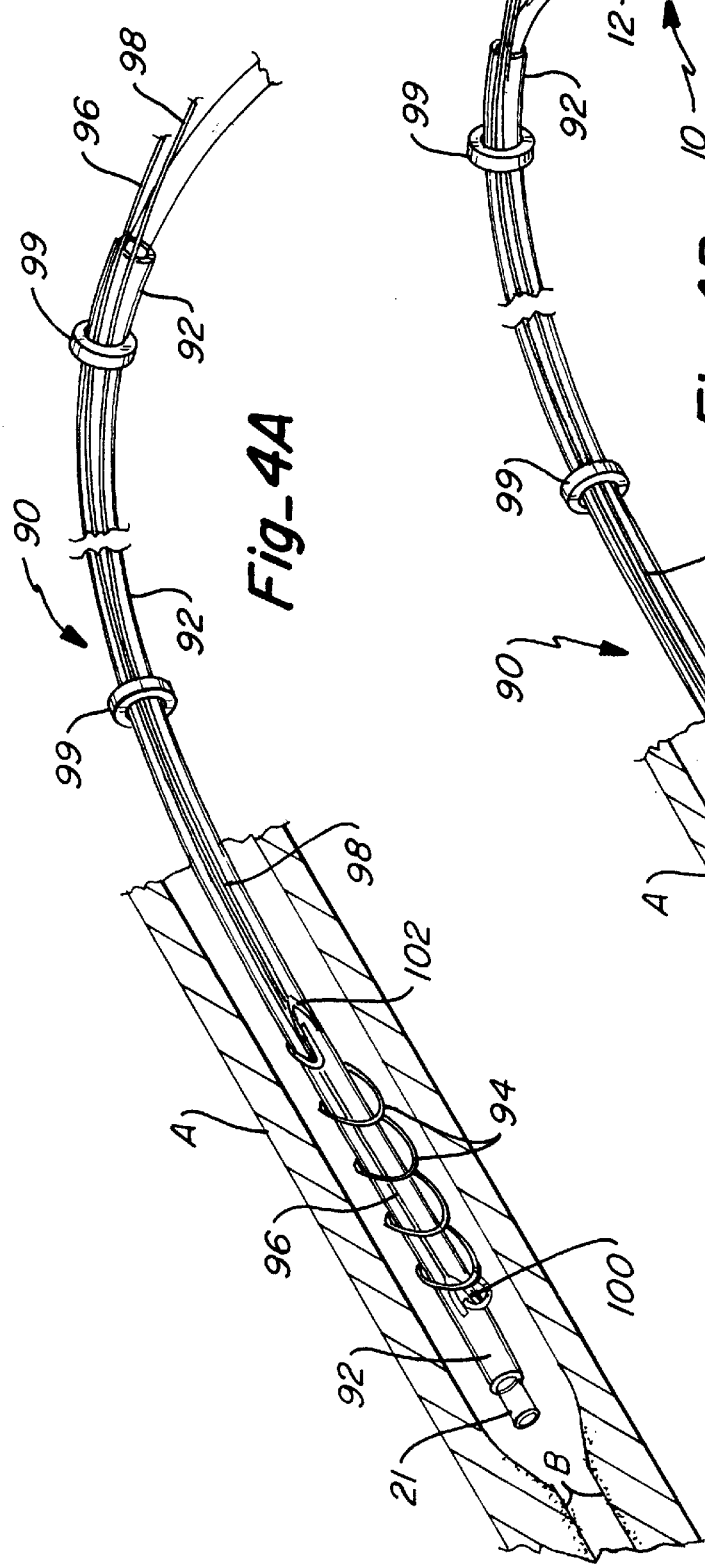

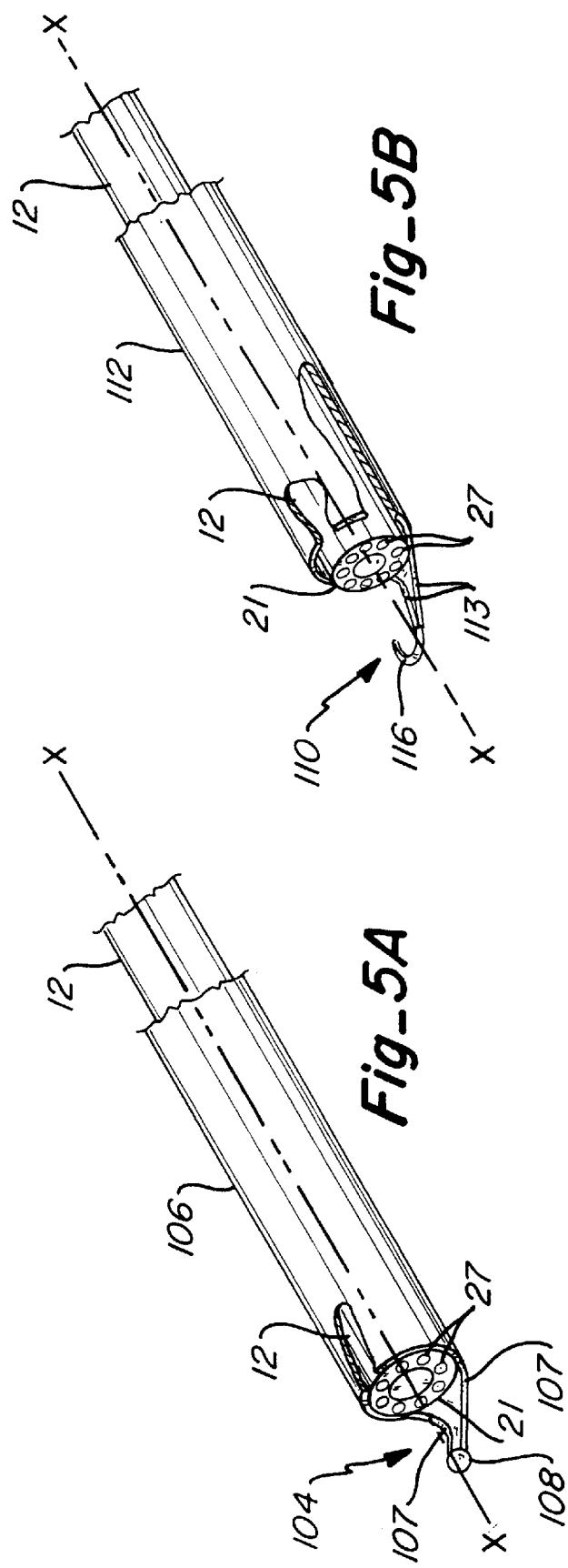

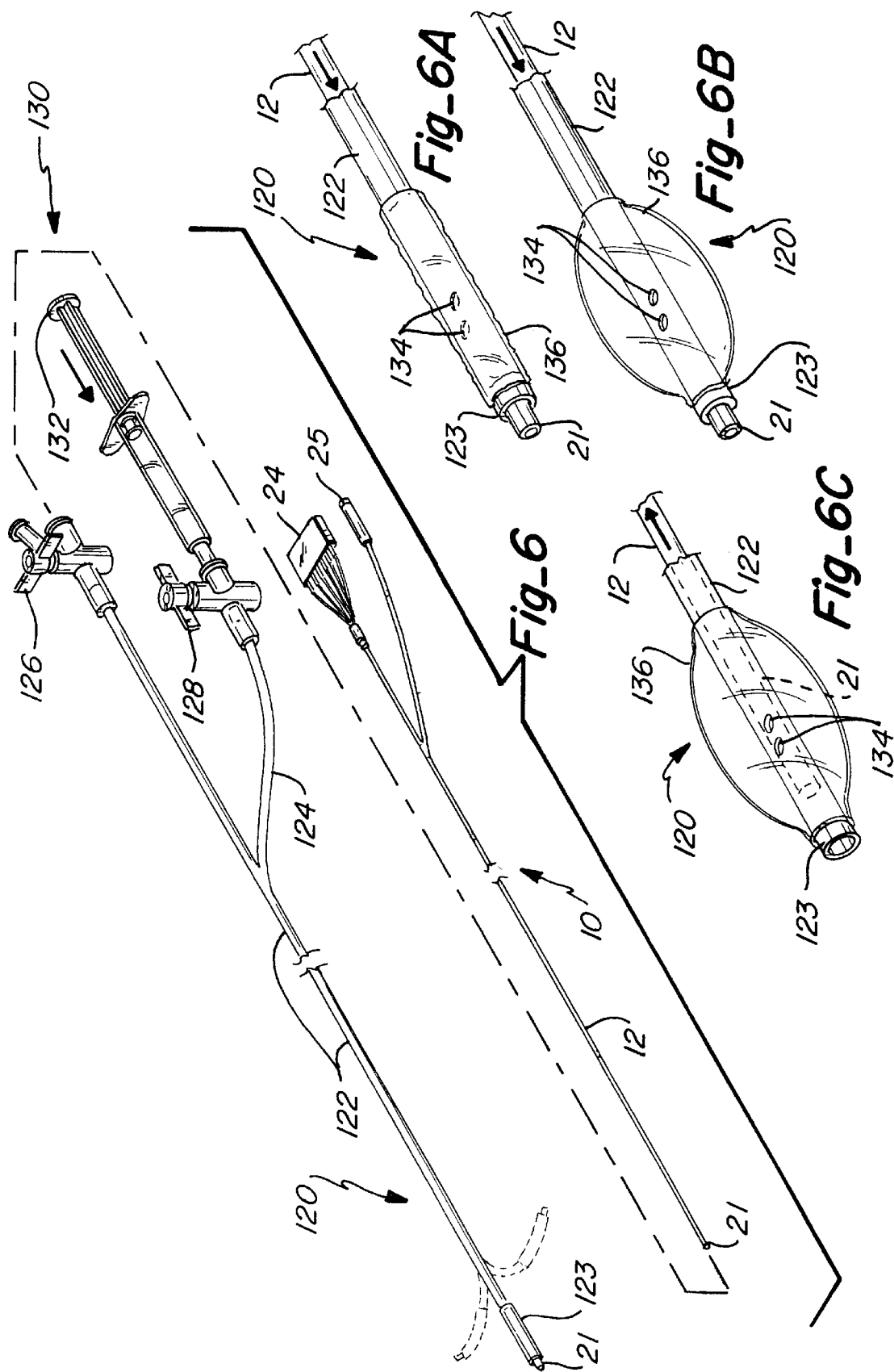

SURGICAL DEVICES WITH REMOVABLE IMAGING CAPABILITY AND METHODS OF EMPLOYING SAME

TECHNICAL FIELD

This invention relates to surgical devices with removable imaging capability and methods of using the same, and more particularly, a microendoscope which may be used in conjunction with traditional surgical instruments which do not have their own integral imaging capability, and methods of employing such a microendoscope in various surgical procedures.

BACKGROUND ART

In recent years, the popularity of endoscopic surgery has proliferated. In fact, it may be accurate to say that endoscopic surgery is now the accepted medical standard for performing many surgical procedures which in past years were not traditionally conducted with endoscopic instruments. A major advantage of endoscopic surgery is that it creates much less trauma for the patient than traditional surgical techniques which required direct visual observation of the site under investigation by the surgeon. Advances have occurred in the electronic industry which allow smaller and smaller endoscopes to be used, thereby permitting endoscopic procedures to be undertaken in a less invasive manner then was previously possible. Also, improved circuitry and optics technology has resulted in enhanced visual imagery by the smaller endoscopes.

However, because of the sophisticated optics and circuitry contained in modern endoscopes, they can be very expensive and difficult to maintain. Additionally, since the size of the endoscope is still a major concern in endoscopic procedures, standard surgical instruments must be modified to reduce their size in order that the instruments can be used simultaneously with the endoscope. For example, it is well-known in the art to provide a plurality of channels within or around the endoscope in order that miniature surgical instruments such as forceps or the like may be simultaneously introduced with the endoscope. Therefore, the construction of most prior art endoscopes begins first with consideration of the size of the endoscope, and then operative channels are formed within or around the endoscope so that the modified surgical instrument may be introduced simultaneously to the site under investigation.

Although great advances have been made in the electronic industry in terms of reducing the size of the imaging elements which are used within the endoscope, many endoscopes in use continue to be too large to conduct certain surgical procedures. Additionally, many surgical procedures cannot be effectively conducted with the miniaturized surgical instruments. Rather, a more fall size surgical instrument is still required. Furthermore, cost continues to be a prohibitive factor because the special surgical instruments must be manufactured which are small enough to fit within the small channels of the endoscope being used.

From the foregoing, it is apparent that an even smaller imaging device is desirable which can be used universally with larger and more standard sized surgical instruments in order to reduce the cost of providing endoscopic capability for certain surgical procedures as well as maintaining a minimally invasive sized instrument with imaging capability which is used to conduct such surgical procedures.

DISCLOSURE OF THE INVENTION

In accordance with the present invention, a microendoscope is provided which may be used with standard surgical instruments which are retrofitted to include a small tube or other means by which the microendoscope may be introduced simultaneously with the standard instruments. The microendoscope of this invention is so small that it by itself presents little or no problem in terms of being an overly invasive object introduced into the surgical area. The microendoscope of this invention can be manufactured with an overall diameter as little as 1 mm. The microendoscope is capable of being manufactured in such a small size by use of either a modified CCD chip or a CMOS-type imaging chip. These imaging chips communicate with circuitry in the form of a miniature circuit board which may be incorporated directly into the microendoscope, is or the circuitry can be located within the video control device remote from the microendoscope. The microendoscope may further include integral light means by which the surgical area under investigation may be illuminated.

In one application, the microendoscope of this invention may be used in conjunction with standard Jackson grasping forceps which have been modified to include a longitudinal tube or channel for which to receive the microendoscope. In use, the microendoscope provides an integral imaging capability while the surgeon manipulates the Jackson grasping forceps for removal of a foreign object within a patient.

In another application, the microendoscope may be used in conjunction with a stent placement catheter. In this application, the microendoscope is placed through the small diameter tube of the catheter to provide integral imaging capability for guiding the catheter to the precise location in the body at which the stent is to be positioned.

In yet another application, the microendoscope of this invention may be used in conjunction with an "over-tube" dissecting or tissue separating device in order to conduct very precise cutting, tissue separating or fulgeration procedures.

In another application, the microendoscope may be used in conjunction with a steerable balloon catheter in much the same manner as the microendoscope is used with the stent placement catheter.

The microendoscope may be sterilized or disinfected in any number of different protocols. The sheath of the microendoscope may be made of a material which can withstand the heat and pressure of an autoclave sterilizing protocol, as well as pure gas or liquid soaking sterilization protocols. Accordingly, the microendoscope may be used numerous times in any number of differing types of surgical instruments in differing kinds of surgical procedures after re-sterilization.

The sheath of the microendoscope also may be very flexible which enables the microendoscope to be twisted or bent in any desired configuration in order to conform to the particular path of the surgical instrument introduced within the patient's body.

These and other advantages will become apparent to those skilled in the art in view of the description of the drawings and the description of the preferred embodiments which follow.

BRIEF DESCRIPTION OF THE DRAWINGS

FIG. 1 is a perspective view of the microendoscope used in conjunction with the surgical devices and methods of this invention, FIG. 2 is an enlarged fragmentary exploded perspective view illustrating the major components of the microendoscope;

FIG. 2A is a longitudinal section taken along line 2A—2A of FIG. 1 illustrating the arrangement of the major components within the microendoscope;

FIG. 3A is a perspective view of the microendoscope used in conjunction with Jackson grasping forceps;

FIG. 3B is a perspective view of a patient undergoing a surgical procedure to remove a foreign object such as a coin from the patient's lungs or trachea by use of the Jackson grasping forceps with imaging capability.

FIG. 4A is an enlarged fragmentary perspective view of the microendoscope used in conjunction with a stent placement catheter;

FIG. 4B is another fragmentary perspective view of the microendoscope used in conjunction with the stent placement catheter wherein the stent placement catheter has been positioned within a desired location within the patient's body and the stent has been activated to allow removal of the catheter and microendoscope;

FIG. 5A is a greatly enlarged fragmentary perspective view of the microendoscope used in conjunction with an over-tube tissue separating device;

FIG. 5B is a fragmentary perspective view of the microendoscope used in conjunction with an over tube dissecting device used for cutting tissue or ligation;

FIG. 6 is a perspective, exploded view of a balloon catheter and the microendoscope prior to its insertion within the catheter;

FIG. 6A is a fragmentary perspective view of the balloon catheter with the microendoscope inserted therethrough prior to inflation of the balloon portion;

FIG. 6B is another fragmentary perspective view of the microendoscope inserted through the balloon catheter after the balloon portion has inflated; and FIG. 6C is yet another fragmentary perspective view as in FIGS. 6A and 6B illustrating the microendoscope being removed from within the balloon catheter.

BEST MODE FOR CARRYING OUT THE INVENTION

FIGS. 1, 2 and 2A illustrate a microendoscope that may be used with any number of different standard sized surgical instruments. The microendoscope 10 includes a sheath 12 which receives and retains therein imaging elements. The imaging elements comprise an imaging sensor or chip such as a CMOS or CCD-type which may be small as 0.50 mm. The size of the CMOS or CCD-type sensor may be varied. For most purposes, although the chip may be made as small as 0.50 mm in diameter, the optimal size would be between 2 to 4 mm with an upper range being from 6 to 10 mm. For most applications, the CMOS-type imaging sensor is more desirable since it can be made in any desired shape. This is because CCD devices have to be made either square or rectangular in shape because the information collected on the pixels of the CCD chip must be transferred and interpreted by the circuitry in a line-by-line fashion, versus a CMOS-type chip which can have its imaging data interpreted pixel by pixel. Typical specifications for the use a CCD-type chip would include one which is approximately ⅛ inch in size and contains an array of pixels of 640×480. In this array and chip size, the pixels would each be approximately 2.4×2.4 microns. One manufacturer for such a small CCD device is the Philips Imaging Technology Company from Eindoven, Netherlands. Other manufacturers which also provide such small type CCD imaging sensors are the Sony Corporation and Panasonic. For the CMOS-type imaging sensor, desirable specifications for this type of imaging sensor would include a CMOS color imager having an array of pixels of 450×350, a spectral response of 350 nanometers to 800 nanometers, a resolution of more than 350 television lines at center, and a minimum illumination of 8 lux at f1.4. Some manufacturers which can provide such a CMOS-type imaging sensor include companies such as VLSI, Inc. of Scotland, Vision, Inc. of San Jose, Calif., Photobit, Inc. of La Crescenta, Calif., and i.e.t., Inc. of Cicero, N.Y. The imaging chip or sensor 16 communicates with a miniature circuit board 14 by means of wires or other appropriate conducting means. The circuit board interprets the images transmitted by the imaging chip, or otherwise conditions the imaging signals so that such signals may be received and viewed on the video control unit 29 via wires or cable 19.

The imaging signals produced by the imaging sensor 16 can be either a digital or analog format. In many instances, the digital format is preferred since it provides the capability to better condition or manipulate the image viewed on a screen. For example, the digital format allows the creation of a number of functions for the image viewed on a screen. Functions such as automatic focus, automatic light control, automatic iris, automatic white balance, and digital recording on compact disks or D.V.D. recording systems are possible.

Although FIG. 2 illustrates the use of one circuit board, it will be understood that a series of circuit boards could be used in order to condition or otherwise manipulate the imaging signals produced by the imaging sensor. Regardless of the number of circuit boards used, they are connected to each other by a series of wire type of conductors or cables which are able to transmit the electronic signals from board to board or from the imaging sensor to the board, if only one board is used. The circuitry in these very small circuit boards can be manufactured to condition the imaging signals produced by the imaging sensors in order to produce the desired visual output on a monitor screen, or may otherwise condition the imaging signals so that they can be recorded in a desired format such as on a compact disk or the like.

The distal end 21 of the microendoscope may be equipped with a desired lens system 20 in order that the surgical area under investigation may be magnified or otherwise conditioned prior to images of the area being received by the chip 16. In addition to or in lieu of a lens system 20, a window 25 may be used to seal the distal end of the microendoscope. The lens system 20 may be movable in front of the imaging sensor, or the imaging sensor 16 and lens system 20 may be bonded together. In either case, the imaging sensor 16 and the lens system 20 are held in a fixed relationship with respect to one another by an outer plastic or metal tube (not shown) which fits over the lens system 20 and the imaging sensor 16. This outer plastic or metal tube may be made of such a diameter or shape that it creates a tight friction fit in holding the lens system 20 and imaging system 16 in place. Alternatively, the chip and lens may also be bonded in place inside the metal or plastic tube by an appropriate adhesive.

The proximal end 23 of the microendoscope 10 may be split into two separate branches and be further equipped in one branch with a video connector 24 which may connect directly to the mother circuit board or corresponding port of a video control unit 29 such as a laptop computer, and the other branch may receive fitting 22 which connects directly to a source of light 28. There is essentially no limit as to the length of the flexible sheath 12. One section of the sheath 12 could be made sterile and have a sufficient length which enabled it to extend out of the sterile field of the surgical area and then connect to the appropriate video control or light sources. The sheath 12 can be made of a rigid material such as stainless steel, aluminum, or rigid plastic tubing made by companies such as the Polygon Company of Walkerton, Ind. Polygon tubing is a material made of a composite plastic and is structurally as strong as many metal materials. Alternatively, the sheath may be made of plastics which are thin-walled and flexible. Using such a flexible material allows for the SASS microendoscope to be both flexible and steerable. Preferable materials for making the microendoscope flexible and steerable include various formulations of teflon®, polyethylene, and polypropylene. Furthermore, if the sheath 12 is made flexible, it can conform to the sharp turns and twists that it may encounter within the body on the path to the desired surgical site.

A plurality of longitudinal channels 26 may be integrally formed within and around the circumference of the sheath 12 which receives a plurality of light fibers 27. The light fibers 27 may extend from fitting 22 all the way to the distal end 21 of the microendoscope in order that the surgical area under investigation may be illuminated. Even with the addition of the longitudinal channels containing the light fibers, the overall diameter D of the microendoscope may be maintained as small as 1 mm.

In addition to light fibers 27, other devices or materials may be passed through these small lumens or channels 26. For example, laser fibers, guide wires, or metallic shaping wires can be placed therein. Malleable wires such as shaping wires may be used in an instance where it is desired to form the microendoscope into a particular shape prior to insertion within a bodily opening. This "shaping" of the endoscope may be particularly useful in the visually aided placement of a device such as an endo-tracheal tube.

The main channel or lumen of the sheath which receives the components of the microendoscope is sealed or bonded to such components so that fluids will not be able to contact the various sensitive electronic elements. For example, an appropriate epoxy can be used to seal the lens system 20 with respect to the interior sides of the sheath which form the main channel or lumen. In addition to making the sheath watertight or fluid resistant, it is desirable to shield the interior electronic components from static or other disruptive electric signals. Therefore, the sheath 12 may be include a braided metal layer (not shown) which effectively shields the electronic components within the sheath from static electricity or other electromagnetic disruptions. This composite sheath or tube protected from static is commonly known in the art as a braided shielded cable. This braided layer may be formed interiorly or exteriorly of the channels 26.

Although the circuit board 14 is illustrated as being inserted within the microendoscope, it shall be understood that the circuit board may be placed within the video control unit 29 or within the video connector 24. In such a circumstance, wires or conductors 18 can be extended the necessary length to link up with the circuit board 14 wherever its particular location. In addition to light fibers 27, fluid or gas can be introduced through one or more of the channels 26 in order to flush or otherwise clear the surgical area.

One method to securely affix the lens system 20 to the sheath, which in turn stabilizes the adjacent electronic components within the sheath, is to drill a plurality of small holes (not shown) within the proximal end of the terminal window 25 which match the spacing and arrangement of longitudinal channels 26. The light fibers are then inserted through the longitudinal channels and into the small holes formed on the terminal window 25. The distal ends of the light fibers 26 are then secured within the holes in the terminal window 25. This traversal of the light fibers actually into the terminal window 25 provides greater strength with respect to the attachment between the sheath and terminal window 25. Furthermore, one or more of metal wires can be placed within one of the channels 26 and inserted within one of the small holes of the terminal window 25 in order to further provide a strong interlock between the sheath 12 and the terminal window 25.

In addition to providing a sterile sheath and extending the length of sheath 12 to ensure that it extends away from the sterile field the desired length, a thin-walled drape (not shown) could be used which is sterile and covers any exposed wiring or cables which are attached to the sheath and which may be in the sterile field. Although not illustrated, it is well understood by those skilled in the art to use a drape which isolates nonsterile components from the sterile field.

The microendoscope 10 will now be described as it is used within a number of differing type of surgical instruments which do not have their own integral imaging capabilities.

The first application of the microendoscope is illustrated in FIGS. 3A and 3B. As shown, the microendoscope 10 may be used with modified Jackson grasping forceps 30. The particular grasping forceps 30 illustrated in FIG. 3A is characterized by an instrument channel 32 which may receive therethrough a pair of elongate grasping tines 34. The grasping tines 34 terminate at the proximal end by forming a single tine rod 35. Grasping tines 34 may be slid inwardly or outwardly within instrument channel 32 by the scissor action of first member 40 and second member 42. The first and second members 40 and 42 connect at pivot point 44. The distal end of second member 42 includes a push link 46 attached thereto at one end by means of pin 50. The other end of push link 46 is connected to bracket 48 by means of pin 52. As rings 56 and 58 of members 42 and 40 are pressed together by the fingers of a surgeon, first member 40 will cause the grasping tines 34 to be moved in a rearward or proximal direction such that the normally separated or open distal ends of tines 34 are pressed or drawn together by their proximal movement into the instrument channel 32. When it is desired to have the tines 34 protrude from the instrument channel 32, rings 56 and 58 are again separated. The forceps are able to grasp a foreign object by the open-close action of the tines 34. Conveniently, tightening knob 54 may be provided so that first member 40 may be positioned at a desired location along tine rod 35. The particular positioning of first member 40 along tine rod 35 enables the grasping tines 34 to protrude a desired distance beyond the distal end of instrument channel 32.

The grasping forceps 30 are modified to include an endoscope tube 36 which receives the microendoscope 10. The tube 36 may be welded or glued alongside channel 32, or attached by other well-known means. Conveniently, the endoscope tube 36 may include a tightening knob or adjustment member 38 to control the extent to which the distal end 21 of the endoscope 10 protrudes beyond the distal end of the endoscope tube 36. Placement of the microendoscope directly alongside the forceps enables the microendoscope to view the tines as they are manipulated to grasp the foreign object. The forward or distal placement of the microendoscope also enables it to view the path of insertion into the patient.

As shown in FIG. 3B, the Jackson grasping forceps are inserted into the patient P to remove a foreign object O which can be viewed on the screen of the video control device 29. From the surgery being performed in FIG. 3B, a foreign object such as a coin may be removed from the lungs or trachea of the patient P by means of the Jackson grasping forceps 30. In the past, an instrument such as a full-sized Jackson grasping forceps could not be introduced simultaneously with an endoscope because the trachea or throat of the patient could not accommodate the simultaneous introduction of both the forceps and the endoscope. Therefore, this procedure previously had to be conducted without the surgeon being able to visualize the Jackson grasping forceps as it was introduced into and through the path in the patient's body prior to reaching the surgical site under investigation. Because of the small size of the microendoscope 10, the addition of endoscope tube 36 makes it possible for the Jackson grasping forceps to have the integral imaging capability. In the operation depicted in FIG. 3B, the Jackson grasping device is the preferred surgical instrument since large objects such as coins require removal by tines of substantial size and strength as found only with such forceps. In other words, smaller forceps which may be introduced through a channel of standard endoscopes do not have the grasping strength or size to hold a relatively large foreign object such as a coin.

FIGS. 4A and 4B illustrate the microendoscope 10 being used in conjunction with a stent placement catheter 90. One common procedure used to dilate or expand a blocked artery A is the introduction of a stent which is used to force open the blockage B. As shown in FIG. 4A, a stent placement catheter assembly 90 may include a catheter tube 92 which is used to transfer a stent coil 94 to the blockage B. The stent coil 94 is wrapped around the exterior walls of the catheter tube 92. A pair of control wires 96 and 98 may connect to the opposite ends of the stent coil 94 at junctions 100 and 102, respectively. Retainers 99 may be used to secure the control wires 96 and 98 to the catheter tube 92. Alternatively, channels (not shown) formed within the walls of the tube 92 may be used to secure the control wires. In prior procedures, the small size of many arteries A prevented the introduction of an endoscope within the artery itself. Accordingly, exact placement of the stent 94 as viewed within the artery was not possible. Because of the small size of the microendoscope 10, it can be placed inside the catheter tube 92 so to provide the surgeon a view of the interior wall of the artery.

In operation, the distal end 21 of the microendoscope may protrude beyond the distal end of the catheter tube 92 in order to provide an image to the surgeon as the stent placement catheter is traversed through the artery or other bodily passages on the route to the artery. As shown in FIG. 4B, once the stent placement catheter has been introduced into the blockage B, the microendoscope may be removed from within the stent placement catheter and the stent coil may be activated to dilate the blockage B. One popular procedure for activating the stent coil 94 is to make the stent from a material such as Nitronol which will remain expanded when activated within the body. Nitronol is a material which is very sensitive to changes in temperature. A low electric current may be introduced through the first and second control wires 96 and 98 in order to heat and, therefore, activate the stent coil 94 so that it uncoils or unravels within the blockage B. Furthermore, the electric current introduced through control wires 96 and 98 will cause the forked ends of junctions 100 and 102 to open thus enabling the control wires to be separated from the opposite ends of the stent coil 94. FIG. 4B illustrates the control wires 96 and 98 being removed after the appropriate electric current has expanded the stent coil 94 and has caused the release of junctions 100 and 102 from the opposite ends of the stent coil 94. After the stent coil has been activated, the catheter may be placed adjacent the coil and the microendoscope may again protrude from the distal end of the catheter enabling the microendoscope to again view the stent to ensure its proper placement.

FIGS. 5A and 5B illustrate another application of the microendoscope 10 with a surgical instrument. As shown in FIG. 5A, a very small diameter over-tube tissue separating device 104 is provided which is characterized by a guide tube 106 which receives the microendoscope. An extension 107 is formed on the distal end of the guide tube 106 to provide a desired separation between the microendoscope 10 and a tissue contacting member. In FIG. 5A, the tissue contacting member is in the form of a separating bead 108. In use, the microendoscope may be introduced into a bodily passage simultaneously with the over-tube separator 104 wherein the separating bead 108 can separate linings of tissue or other discrete delineations between tissue types so that a subsequent surgical procedure can take place at the location of the separated tissues. Because of the extremely small size of the microendoscope, the separating bead 108 can be used in the most delicate separating procedures. The guide tube 106 is preferably rigid and may extend any desired length depending upon the particular bodily passage within which the separator 104 is to be introduced.

FIG. 5B illustrates one modification of the over-tube separator 104. As shown in FIG. 5B, the over-tube device may take the form of an over-tube dissector 110 which also includes a guide tube 112 and an extension 113. In lieu of the separating bead 108, the extension 113 may have attached thereto a dissecting hook 116 which can be used to separate, cut, or otherwise manipulate tissue in a desired location. As further shown in FIG. 5B, the distal end of the microendoscope 21 may protrude beyond the distal end of the guide tube 112. Alternatively, as shown in FIG. 5A, an adequate visual image of the area under investigation may be achieved by having the distal end of the microendoscope 21 positioned flush with the distal end of the guide tube 106. Although not illustrated, the over-tube dissector could also include an electrode positioned adjacent to or in lieu of the separating bead 108 or hook 116. Such an electrode could be charged with an electric current to fulgerate tissue at a desired area.

In yet another application, the microendoscope 10 may be used in conjunction with a balloon catheter 120. The balloon catheter 120 shown in FIG. 6 is of a type used within very small bodily passages such as the urethra or the like. The balloon catheter 120 may include an elongate guide tube 122 having a distal end 123 which may be non-steerable, or steerable by guide wires (not shown) and a steering unit (not shown) which controls the guide wires as understood by those skilled in the art. The free or proximal end of air inflation port 124 connects to stop cock 128 which in turn connects to syringe 130. A very small diameter air inflation line (not shown) may be formed interiorly of guide tube 122 and connect between port 124 and openings 134. When the plunger 132 of the syringe is depressed, air is forced through air inflation port 124, through the small inflation line (not shown) and through openings 134 to inflate the balloon 136. Stop cock 128 may be positioned to prevent the back flow of air into the syringe 130 thus keeping the balloon inflated. As also shown in FIG. 6, guide tube 122 may further include its own stop cock 126 positioned at the proximal end thereof in order that the guide tube 122 may also introduce liquids or gas simultaneously with the endoscope. Supply tubes (not shown) can supply the appropriate liquids or gas through stop cock 126.

The sequential operation of the balloon catheter will now be explained with reference to FIGS. 6A–6C. First, the microendoscope 10 is inserted through the guide tube 122. The distal end 21 of the microendoscope may protrude beyond the distal end 123 of the guide tube 122 as shown in FIG. 6A. The catheter is then inserted into the body of a patient. As the balloon catheter is traversed through the desired bodily passage, the microendoscope 10 can provide a continuous image of the path of traversal. When the distal end of the balloon catheter reaches its desired destination, balloon 136 may be inflated as illustrated in FIG. 6B. As shown in FIG. 6C, the microendoscope may then be withdrawn back through the guide tube 122. The desired surgical procedure may then take place by the introduction of a desired instrument through the guide tube 122.

By the foregoing, it is apparent that many surgical procedures can be enhanced by the use of a very small microendoscope which provides an integral imaging capability to the surgeon. Relatively large surgical instruments such as Jackson grasping forceps may be provided with their own integral imaging capability by the attachment of the microendoscope. The introduction of stents into arteries may now be achieved with direct view of the blockage by the microendoscope which is introduced simultaneously with the catheter. In procedures where tissue must be separated or dissected, very precise tissue manipulation can occur by use of an over-tube device which is placed directly over the microendoscope. In yet another application, the use of a balloon catheter may be enhanced by the microendoscope which is again introduced simultaneously with the catheter.

This invention has been described in detail with reference to particular embodiments thereof, but it will be understood that various other modifications can be effected within the spirit and scope of this invention.

What is claimed is:

1. A surgical device with removable imaging capability for use at a surgical site, said surgical device comprising:

a microendoscope including an elongate sheath having a peripheral wall and a central passageway formed therethrough, an imaging sensor placed within said central passageway at a distal end of said sheath, circuitry means placed adjacent said imaging sensor at said distal end and extending along said central passageway such that said circuitry means does not extend circumferentially beyond said imaging sensor, conducting means interconnecting said imaging sensor to said circuitry means for transferring electrical signals from said imaging sensor to said circuitry means, and a conductor interconnecting said circuitry means for providing a video ready signal to a video control device which enables a viewer to view visual images captured by said imaging sensor of the surgical site;

grasping forceps including an instrument channel having a central opening formed therethrough, grasping tines having proximal ends connected to one another and distal ends spaced apart a desired distance, said proximal ends being inserted through said central opening, a first member having a distal end attached to said proximal ends of said grasping tines, a second member having a distal end attached to said instrument channel and said second member being pivotally connected to said first member, said first member being movable with respect to said second member to move said grasping tines longitudinally within said instrument channel to cause said distal ends of said grasping tines to be pressed together when entering said central opening or to be spaced apart when exiting said central opening; and an endoscope tube attached exteriorly of said instrument channel for receiving said microendoscope such that said microendoscope may provide a visual image as said grasping forceps are manipulated within the body of a patient.

2. A device, as claimed in claim 1, farther including:

a lens within said passageway of said elongate sheath to condition the image of the surgical site prior to being received by said imaging sensor.

3. A device, as claimed in claim 1, further including:

a plurality of longitudinal channels formed within said peripheral wall of said elongate sheath; and at least one light fiber in one of said plurality of longitudinal channels and extending to said distal end of said elongate sheath, said light fiber communicating with a source of light to illuminate the surgical area under observation.

4. A surgical device with removable imaging capability for use at a surgical site, said surgical device comprising:

a microendoscope including an elongate sheath having a peripheral wall and a central passageway formed therethrough, an imaging sensor placed within said central passageway at a distal end of said sheath, processor circuitry means placed adjacent said imaging sensor at said distal end and extending along said central passageway such that said circuitry means does not extend circumferentially beyond said imaging sensor, conducting means interconnecting said imaging sensor to said processor circuitry means for transferring electrical signals from said imaging sensor to said processor circuitry means, and a conductor directly interconnecting said processor circuitry means for providing a video ready signal to a video control device which enables a viewer to view visual images captured by said imaging sensor of the surgical site; and a stent placement catheter including a tube having a central opening formed therethrough, a stent coil positioned at a distal end of said tube and exteriorly thereof, at least one control wire connected to said stent coil, said at least one control wire extending longitudinally along said tube, said microendoscope being insertable through said central opening such that said microendoscope may provide a visual image as said catheter is manipulated within the body of a patient.

5. A device, as claimed in claim 4, further including:

a lens within said passageway of said elongate sheath to condition the image of the surgical site prior to being received by said imaging sensor.

6. A device, as claimed in claim 4, further including:

a plurality of longitudinal channels formed within said peripheral wall of said elongate sheath; and at least one light fiber in one of said plurality of longitudinal channels and extending to said distal end of said elongate sheath, said light fiber communicating with a source of light to illuminate the surgical area under observation.

7. A surgical device with removable imaging capability for use at a surgical site, said surgical device comprising:

a microendoscope including an elongate sheath having a peripheral wall and a central passageway formed therethrough, an imaging sensor placed within said central passageway at a distal end of said sheath, circuitry means placed adjacent said imaging sensor at said distal end and extending along said central passageway such that said circuitry means does not extend circumferentially beyond said imaging sensor, conducting means interconnecting said imaging sensor to said circuitry means for transferring electrical signals from said imaging sensor to said circuitry means, and a conductor interconnecting said circuitry means for providing a video ready signal to a video control device which enables a viewer to view visual images captured by said imaging sensor of the surgical site; and an over-tube device including a guide tube having a central opening formed therethrough, an extension connected to a distal end of said over-tube device and extending distally thereof, and a tissue contacting member attached to said extension for manipulating the tissue of a patient, said microendoscope being insertable through said central opening enabling said microendoscope to view said tissue contacting member and the surrounding surgical area as tissue manipulation occurs.

8. A device, as claimed in claim 7, further including:

a lens within said passageway of said elongate sheath to condition the image of the surgical site prior to being received by said imaging sensor.

9. A device, as claimed in claim 7, further including:

a plurality of longitudinal channels formed within said peripheral wall of said elongate sheath; and at least one light fiber in one of said plurality of longitudinal channels and extending to said distal end of said elongate sheath, said light fiber communicating with a source of light to illuminate the surgical area under observation.

10. A device, as claimed in claim 7, wherein said tissue contacting member is a separating bead having a spherical shape especially adapted for tissue separation.

11. A device, as claimed in claim 7, wherein said tissue contacting member is a hook-shaped structure enabling tissue cutting.

12. A surgical device with removable imaging capability for use at a surgical site, said surgical device comprising:

a microendoscope including an elongate sheath having a peripheral wall and a central passageway formed therethrough, an imaging sensor placed within said central passageway at a distal end of said sheath, processor circuitry means placed adjacent said imaging sensor at said distal end and extending along said central passageway such that said circuitry means does not extend circumferentially beyond said imaging sensor, conducting means interconnecting said imaging sensor to said processor circuitry means for transferring electrical signals from said imaging sensor to said processor circuitry means, and a conductor directly interconnecting said processor circuitry means for providing a video ready signal to a video control device which enables a viewer to view visual images captured by said imaging sensor of the surgical site; and a balloon catheter including a guide tube having a distal end, a periphery, and a central opening formed therethrough, a balloon attached around said distal end and said periphery of said guide tube, at least one hole formed through said distal end of said guide tube, a means to introduce gas through said at least one hole, said introducing means communicating with a source of air to inflate said balloon, wherein said microendoscope is insertable through said central opening to enable the microendoscope to provide a visual image as said balloon catheter is manipulated within the body of a patient.

13. A device, as claimed in claim 12, further including:

a lens within said passageway of said elongate sheath to condition the image of the surgical site prior to being received by said imaging sensor.

14. A device, as claimed in claim 12, further including:

a plurality of longitudinal channels formed within said peripheral wall of said elongate sheath; and at least one light fiber in one of said plurality of longitudinal channels and extending to said distal end of said elongate sheath, said light fiber communicating with a source of light to illuminate the surgical area under observation.

15. A device, as claimed in claim 12, further including:

a stop cock placed in line with said introducing means to control flow of air through said at least one hole.

16. A method of placing a stent at a desired site within the body of a patient, said method comprising the steps of:

providing a catheter including a central opening and a stent attached at the distal end of the catheter;

inserting a microendoscope through the central opening of the catheter, said microendoscope including an elongate sheath having a peripheral wall and a central passageway formed therethrough, an imaging sensor placed within said central passageway at a distal end of said sheath, processor circuitry means placed adjacent said imaging sensor at said distal end and extending along said central passageway such that said circuitry means does not extend circumferentially beyond said imaging sensor, conducting means interconnecting said imaging sensor to said processor circuitry means for transferring electrical signals from said imaging sensor to said processor circuitry means, and a conductor directly interconnecting said processor circuitry means for providing a video ready signal to a video control device which enables a viewer to view visual images captured by said imaging sensor of the surgical site;

inserting the catheter containing the microendoscope into the body of a patient;

viewing the body of the patient by images produced from the microendoscope as the catheter is moved therethrough;

locating the desired site to which the stent is to be placed by means of the images produced from the microendoscope;

activating the stent at the desired site; and withdrawing the catheter and microendoscope from within the body of the patient.

17. A method, as claimed in claim 16, further including the step of:

recording the images produced from the microendoscope by means of a computer.

18. A method of placing a balloon catheter at a desired location within the body of a patient, said method comprising the steps of:

providing a catheter having a central opening and a balloon attached to a distal end of the catheter;

inserting a microendoscope through the central opening of the catheter, said microendoscope including an elongate sheath having a peripheral wall and a central passageway formed therethrough, an imaging sensor placed within said central passageway at a distal end of said sheath, processor circuitry means placed adjacent said imaging sensor at said distal end and extending along said central passageway such that said circuitry means does not extend circumferentially beyond said imaging sensor, conducting means interconnecting said imaging sensor to said processor circuitry means for transferring electrical signals from said imaging sensor to said processor circuitry means and a conductor directly interconnecting said processor circuitry means for providing a video ready signal to a video control device which enables a viewer to view visual images captured by said imaging sensor of the surgical site;

inserting the catheter containing the microendoscope within the body of the patient;

viewing the body of the patient as the catheter is moved through the body by means of visual images produced from the microendoscope;

locating the desired surgical area by means of the images produced from the microendoscope;

activating the balloon of the balloon catheter within a bodily passage of the patient at the desired surgical area;

withdrawing the microendoscope from within the central opening of the balloon catheter; and introducing a surgical instrument through the central opening of the balloon catheter and to the desired surgical area to conduct a surgical procedure.

19. A method, as claimed in claim 18, further including the step of:

recording the images produced from the microendoscope by means of a computer.

* * * * *